US007003347B2

(12) United States Patent
Stahmann

(10) Patent No.: US 7,003,347 B2
(45) Date of Patent: Feb. 21, 2006

(54) SYSTEM AND METHOD FOR CARDIAC RHYTHM MANAGEMENT WITH DYNAMICALLY ADJUSTED SYNCHRONIZED CHAMBER PACING PROTECTION PERIOD

(75) Inventor: Jeffrey E. Stahmann, Ramsey, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 602 days.

(21) Appl. No.: 10/172,380

(22) Filed: Jun. 14, 2002

(65) Prior Publication Data

US 2003/0028222 A1 Feb. 6, 2003

Related U.S. Application Data

(63) Continuation-in-part of application No. 09/748,754, filed on Dec. 26, 2000, now Pat. No. 6,829,505.

(51) Int. Cl.
*A61N 1/368* (2006.01)

(52) U.S. Cl. .................. 607/9; 607/4; 607/14; 607/25

(58) Field of Classification Search .................. 607/9, 607/4, 15, 14, 25; 600/509, 510, 516, 521
See application file for complete search history.

(56) References Cited

U.S. PATENT DOCUMENTS

| 4,407,287 | A | * | 10/1983 | Herpers .......................... 607/9 |
| 5,105,809 | A | * | 4/1992 | Bach et al. ...................... 607/5 |
| 5,129,393 | A | | 7/1992 | Brumwell ............. 128/419 PG |
| 5,174,289 | A | | 12/1992 | Cohen .................. 128/419 PG |
| 5,267,560 | A | | 12/1993 | Cohen ........................... 607/25 |
| 5,514,161 | A | | 5/1996 | Limousin ........................ 607/9 |
| 5,584,867 | A | | 12/1996 | Limousin et al. .............. 607/9 |
| 5,674,259 | A | | 10/1997 | Gray ............................ 607/20 |
| 5,782,887 | A | * | 7/1998 | van Krieken et al. ......... 607/25 |
| 5,902,324 | A | | 5/1999 | Thompson et al. ............. 607/9 |
| 5,935,160 | A | | 8/1999 | Auricchio et al. ........... 607/122 |
| 5,941,830 | A | * | 8/1999 | Williams ..................... 600/509 |
| 6,070,101 | A | * | 5/2000 | Struble et al. .................. 607/9 |
| 6,081,748 | A | | 6/2000 | Struble et al. .................. 607/9 |
| 6,122,545 | A | | 9/2000 | Struble et al. .................. 607/9 |
| 6,128,535 | A | | 10/2000 | Maarse ......................... 607/28 |
| 6,169,918 | B1 | | 1/2001 | Haefner et al. ............. 600/509 |
| 6,188,926 | B1 | | 2/2001 | Vock |
| 6,198,968 | B1 | * | 3/2001 | Prutchi et al. .................. 607/9 |
| 6,240,313 | B1 | | 5/2001 | Esler ........................... 600/516 |
| 6,263,242 | B1 | | 7/2001 | Mika et al. ..................... 607/9 |

(Continued)

OTHER PUBLICATIONS

Kramer, Andrew P., et al., "Apparatus and Method for Reversal of Myocardial Remolding with Electrical Stimulation", U.S. Appl. No. 09/884,256, (Apr. 27, 2001),19 pgs.

(Continued)

*Primary Examiner*—Kennedy Schaetzle
*Assistant Examiner*—John D. Alexander
(74) *Attorney, Agent, or Firm*—Schwegman, Lundberg, Woessner & Kluth, P.A.

(57) ABSTRACT

A device and method for cardiac rhythm management in which one heart chamber, designated as the synchronized chamber, is paced in accordance with a pacing mode that employs sense signals from the opposite chamber, designated as the rate chamber. A synchronized chamber protection period triggered by an intrinsic or paced beat in the synchronized chamber is used to inhibit pacing without otherwise disturbing the pacing algorithm. The duration of the synchronized chamber protection period is dynamically adjusted based upon detection of a repolarization in the synchronized chamber

27 Claims, 10 Drawing Sheets

U.S. PATENT DOCUMENTS

| | | | |
|---|---|---|---|
| 6,285,907 B1 | 9/2001 | Kramer et al. | 607/9 |
| 6,317,631 B1 | 11/2001 | Ben-Haim et al. | 607/9 |
| 6,370,430 B1 | 4/2002 | Mika et al. | 607/9 |
| 6,411,848 B1 | 6/2002 | Kramer et al. | 607/9 |
| 6,421,564 B1 | 7/2002 | Yerich et al. | 607/9 |
| 6,424,866 B1 | 7/2002 | Mika et al. | 607/9 |
| 6,438,421 B1 | 8/2002 | Stahmann et al. | 607/9 |
| 6,456,878 B1 | 9/2002 | Yerich et al. | 607/9 |
| 6,456,880 B1 | 9/2002 | Park et al. | 607/25 |
| 6,466,820 B1 * | 10/2002 | Juran et al. | 607/9 |
| 6,477,415 B1 | 11/2002 | Yerich et al. | 607/9 |
| 6,477,417 B1 | 11/2002 | Levine | 607/9 |
| 6,496,730 B1 | 12/2002 | Juran et al. | 607/9 |
| 6,501,988 B1 | 12/2002 | Kramer et al. | 607/9 |
| 6,512,952 B1 | 1/2003 | Stahmann et al. | 607/9 |
| 6,512,953 B1 | 1/2003 | Florio et al. | 607/28 |
| 6,522,921 B1 | 2/2003 | Stahmann et al. | 607/9 |
| 6,522,923 B1 | 2/2003 | Turcott | 607/27 |
| 6,829,505 B1 | 12/2004 | Kramer et al. | |
| 2005/0065565 A1 | 3/2005 | Kramer et al. | |

OTHER PUBLICATIONS

Kramer, Andrew P., et al., "System and Method for Cardiac Rhythm Management with Synchronized Pacing Protection Period", U.S. Appl. No. 09/748,754 Co-Pending Application, (Dec. 26, 2000),31 pgs.

* cited by examiner

SYSTEM AND METHOD FOR CARDIAC RHYTHM MANAGEMENT WITH DYNAMICALLY ADJUSTED SYNCHRONIZED CHAMBER PACING PROTECTION PERIOD

CROSS-REFERENCE TO RELATED APPLICATION(S)

This is a continuation-in-part of U.S. patent application Ser. No. 09/748,754, filed on Dec. 26, 2000, now issued as U.S. Pat. No. 6,829,505 and entitled "System and Method for Cardiac Rhythm Management with Synchronized Pacing Protection Period," the disclosure of which is hereby incorporated by reference.

FIELD OF THE INVENTION

This invention pertains to methods and apparatus for cardiac rhythm management. In particular, the invention relates to methods and apparatus for providing cardiac resynchronization therapy.

BACKGROUND

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as the delivery cardioversion or defibrillation shocks to terminate atrial or ventricular fibrillation.)

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Patients with conventional pacemakers can also have compromised cardiac output because artificial pacing with an electrode fixed into an area of the myocardium does not take advantage of the above-described specialized conduction system. The spread of excitation from a single pacing site must proceed only via the much slower conducting muscle fibers of either the atria or the ventricles, resulting in the part of the myocardium stimulated by the pacing electrode contracting well before parts of the chamber located more distally to the electrode, including the myocardium of the chamber contralateral to the pacing site. Although the pumping efficiency of the heart is somewhat reduced from the optimum, most patients can still maintain more than adequate cardiac output with artificial pacing.

Heart failure is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium as described above. The resulting diminishment in cardiac output may be significant in a CHF patient whose cardiac output is already compromised. Intraventricular and/or interventricular conduction defects are also commonly found in CHF patients. In order to treat these problems, cardiac rhythm management devices have been developed which provide electrical pacing stimulation to one or more heart chambers in an attempt to improve the coordination of atrial and/or ventricular contractions, termed cardiac resynchronization therapy.

SUMMARY OF THE INVENTION

The present invention relates to a device and method for cardiac rhythm management in which one heart chamber or cardiac site, designated as the synchronized chamber or site, is paced in accordance with a pacing mode that employs sense signals from the opposite chamber or another cardiac site, designated as the rate chamber or site. In order to prevent a pace from being delivered to the synchronized chamber or site during the vulnerable period when the chamber or cardiac site is repolarizing, a synchronized chamber protection period triggered by an intrinsic or paced beat in the synchronized chamber is used to inhibit pacing of the synchronized chamber without otherwise disturbing the pacing algorithm. In accordance with the invention, the duration of the synchronized chamber protection period is dynamically adjusted based upon detection of a repolarization in the synchronized chamber

DESCRIPTION OF THE INVENTION

Figure 1A:
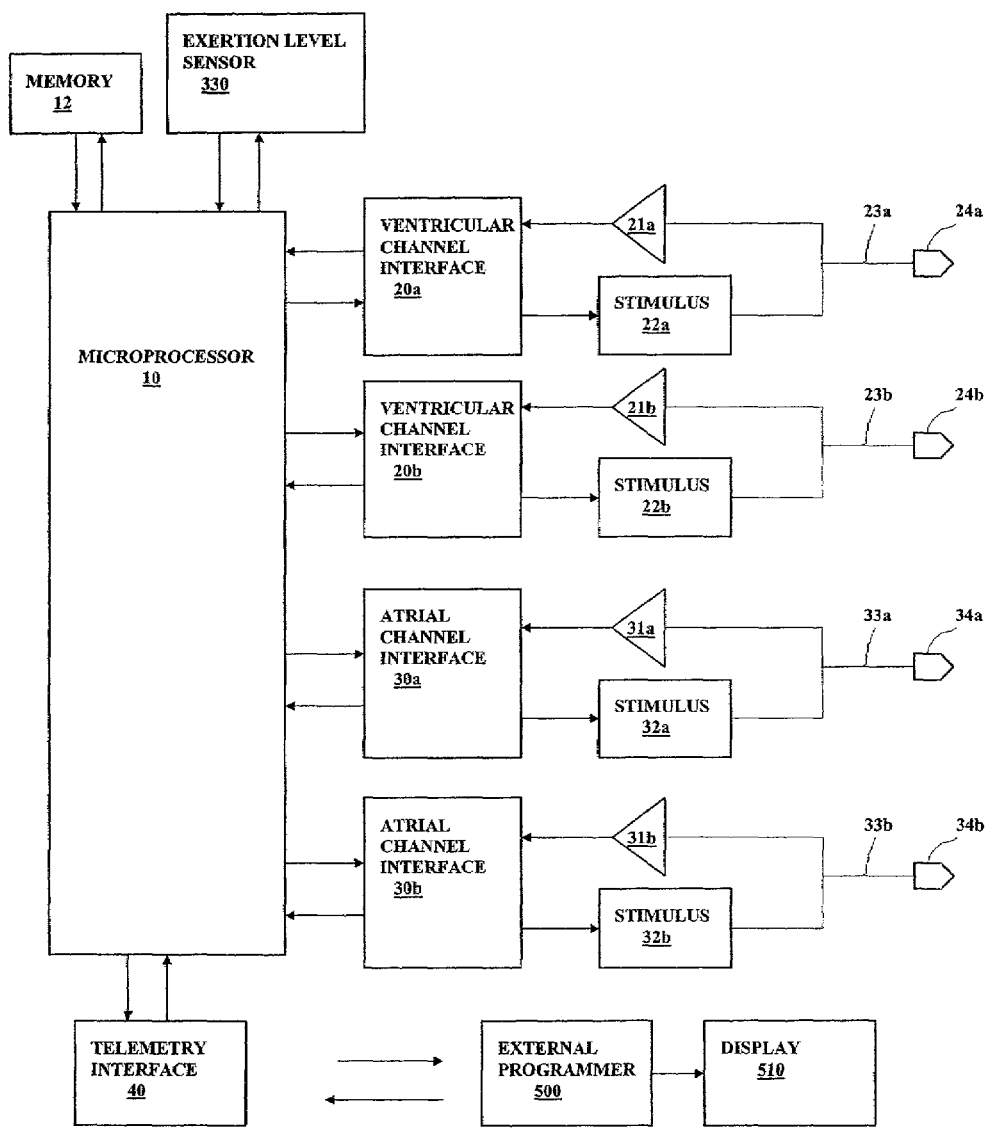
FIGS. 1A and 1B illustrate system-level components of a pacemaker configured for biventricular pacing and sensing.

Cardiac resynchronization therapy can most conveniently be delivered by a cardiac rhythm management device in accordance with a bradycardia pacing mode so that the activation patterns between and within selected heart chambers are both resynchronized and paced concurrently. In the resynchronization pacing modes described herein, one heart chamber, designated as the rate chamber, is paced with a bradycardia mode while the contralateral chamber or other pacing site, designated as the synchronized chamber or synchronized site, is paced with a synchronized pacing mode based upon senses and paces occurring in the rate chamber. For example, the right ventricle may be designated the rate chamber and the left ventricle designated as the synchronized chamber so that paces are delivered to both ventricles based upon right ventricular senses and paces.

Heart muscle contracts when it becomes electrically depolarized, and relaxes as it repolarizes and prepares for the next contraction. The time during which the heart remains depolarized, or depolarization interval, corresponds to the action potential durations of the individual muscle fibers. During the period in which heart muscle is repolarizing after a depolarizing contraction, the heart is in a vulnerable period in which an electrical stimulus delivered at that time may trigger an arrhythmia such as fibrillation. In a synchronous resynchronization pacing mode, paces to the rate chamber are only delivered at a pacing instant that occurs upon expiration of an escape interval that starts with a rate chamber sense and is reset by a subsequent rate chamber sense. Because the escape interval can be selected to be greater than any possible depolarization interval, the rate chamber is protected from receiving a pace during its vulnerable period.

A problem that arises when a pacing instant for a synchronized heart chamber or other synchronized site is based upon whether or not a sense signal is received only from the contralateral rate chamber (or distant rate site within the same chamber as the synchronized site) is that the risk of a pace being delivered near the time of a prior contraction and during the vulnerable period is increased. This is because the pacing of a synchronized site is neither inhibited nor triggered by intrinsic activity at that site, which activity may occur sooner or later than that of the rate site during a particular cardiac cycle. In order to protect the synchronized chamber from being paced during its vulnerable period, the present invention provides a synchronized chamber protection period that is initiated by a sense or pace in the synchronized chamber. During the synchronized chamber protection period, any scheduled pace to the synchronized chamber is inhibited in a manner that does not otherwise disturb the pacing algorithm.

The synchronized chamber protection period may begin after a synchronized chamber sense or pace and be set to a programmed value that corresponds to the maximum expected depolarization interval. Alternatively, the synchronized chamber protection period can be a time window that starts after a synchronized chamber or pace at the earliest expected time of repolarization and lasts until the latest expected time of repolarization. Implementing a synchronized chamber protection period as a fixed time interval, however, must necessarily be overinclusive in order to achieve adequate protection. This limits the effectiveness of the pacemaker since it means that some paces to the synchronized chamber or site will be inhibited when they could have been safely delivered. Also, even if the synchronized chamber protection period is initially set to the most appropriate value, the patient's condition may change over time. To overcome these limitations, the synchronized chamber protection period may be dynamically adjusted in accordance with sensed repolarizations in the synchronized chamber.

In one embodiment of the invention, a repolarization in the synchronized chamber is sensed after a synchronized chamber sense or pace in order to measure the depolarization interval, and the synchronized chamber protection period is then set to approximately equal the depolarization interval with a possible added safety margin. Since the depolarization interval may differ depending upon whether the depolarization of the chamber is due to a sense or a pace, separate measurements for intrinsic and paced depolarizations may be performed. The synchronized chamber protection period is then set to approximately equal the intrinsic depolarization interval after a synchronized chamber sense and to approximately equal the paced depolarization interval after a synchronized chamber pace. Intrinsic and paced depolarization intervals of heart muscle may also vary with heart rate. In another embodiment, separate measurements of intrinsic and paced depolarization intervals are taken for a plurality of different heart rates and then associated with different heart rate ranges. The synchronized chamber protection period is then set equal to the intrinsic or paced depolarization interval associated with the currently measured heart rate. Whichever of the methods just described are used to measure a depolarization interval and accordingly set the synchronized chamber protection period, a measurement of the depolarization interval may be performed once to obtain a nominal value, performed periodically to continually update the measurement, or performed for a number of cardiac cycles to obtain an average value.

In another embodiment for dynamically adjusting the synchronized chamber protection period, the synchronized chamber protection period is adjusted after each sense or pace in the synchronized chamber so as to last until a repolarization in the synchronized chamber is detected. Thus, the synchronized chamber protection period is adjusted to just cover the vulnerable period during each cardiac cycle. In the situation where no repolarization is detected after a synchronized chamber sense or pace, the synchronized chamber protection period can revert to a default value in order to protect against undersensing of a repolarization.

1. Hardware Platform

Pacemakers are usually implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

FIG. 1A shows a system diagram of a microprocessor-based pacemaker physically configured with sensing and pacing channels for both atria and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels for both atria comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20a–b and 30a–b include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. An exertion level sensor 330 (e.g., an accelerometer, a minute ventilation sensor, or other sensor that measures a parameter related to metabolic demand) enables the controller to adapt the pacing rate in accordance with changes in the patient's physical activity. A telemetry interface 40 is also provided for communicating with an external programmer 500 which has an associated display 510.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

Figure 1B:
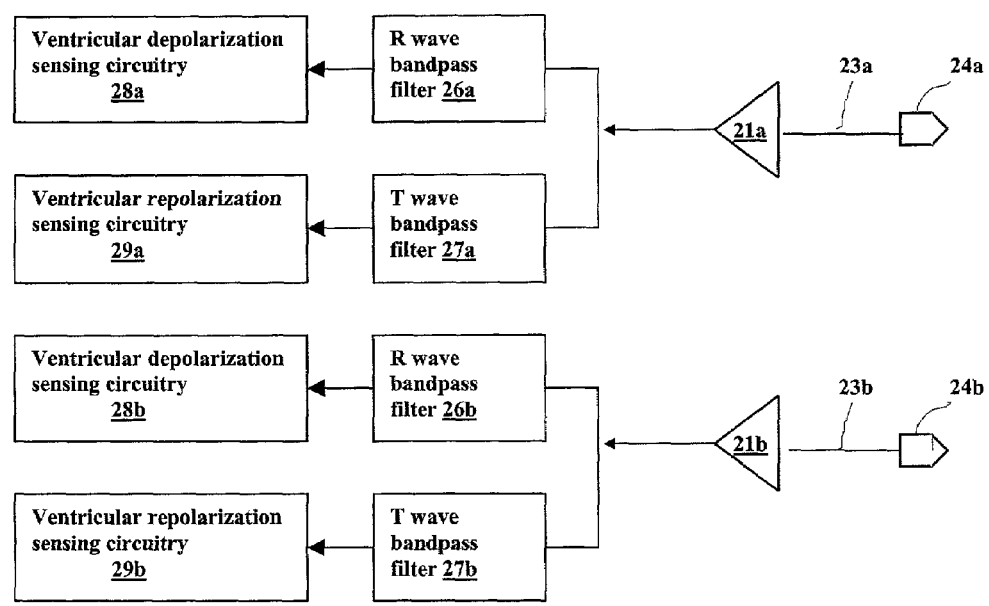

As discussed above, the present invention involves the adjustment of a synchronized chamber protection period based upon detection of ventricular repolarizations, either to measure the length of a depolarization interval or to directly set the length of the protection period. The atrial and ventricular sensing channels can be designed to detect both depolarizations (i.e., atrial or ventricular senses) and repolarizations. FIG. 1B illustrates how this may be implemented in the ventricular sensing channels. When the channel is awaiting a ventricular sense, the electrogram signal is passed through an R wave bandpass filter (26a or 26b) with passband characteristics selected to match the frequency content of a ventricular depolarization. The ventricular depolarization sensing circuitry (28a or 28b) then compares the filtered electrogram signal with a threshold to detect when a ventricular sense occurs. After a ventricular sense occurs, the channel awaits a ventricular repolarization during a specified time frame (e.g., between 50 and 500 milliseconds after the ventricular depolarization). During this time, the electrogram signal is passed through a T wave bandpass filter (27a or 27b) that has a passband characteristic conforming to the frequency content of a ventricular repolarization which is generally lower than that of a ventricular depolarization. The ventricular repolarization sensing circuitry (29a or 29b) then compares the filtered electrogram signal with a threshold to determine when the repolarization occurs. The channel may continue to monitor for depolarizations during this time in case the repolarization is undersensed. A similar scheme with atrial depolarization and repolarization bandpass filters and sensing circuits may be implemented to detect atrial repolarizations.

The bandpass filters in FIG. 1B may be implemented as analog filters that operate directly on the electrogram signal received from the electrodes or may be switched capacitor-type filters that sample the electrogram signal into a discrete-time signal which is then filtered. Alternatively, the electrogram signal can be sampled and digitized by an A/D converter in the channel interface with the bandpass filtering implemented in the digital domain by a dedicated processor or code executed by the controller 10.

2. Bradycardia Pacing Modes

Bradycardia pacing modes refer to pacing algorithms used to pace the atria and/or ventricles when the intrinsic atrial and/or ventricular rate is inadequate due to, for example, sinus node dysfunction or AV conduction blocks. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrioventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which intrinsic atrial rates are unreliable or pathological. In a rate-adaptive pacemaker, for example, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrial or intra-ventricular conduction delays by delivering paces to multiple sites of the chamber.

Other therapeutic alterations of cardiac function through multisite pacing changes in activation and contraction sequences are included in the meaning of cardiac resynchronization therapy. For instance, pacing at more than one site within a heart chamber to desynchronize the contraction sequence of that chamber may be therapeutic in patients with hypertrophic obstructive cardiomyopathy, where creating asynchronous contractions with multi-site pacing reduces the abnormal hyper-contractile function of the chamber. Similarly altering bilateral contraction sequences or intrachamber contraction sequences by pre-exciting one site relative to another site may be used to alter the regional workload and metabolic energy demand of the pre-excited region in order to allow regions of damaged heart tissue to recover from injury or disease.

It is advantageous to deliver resynchronization therapy in conjunction with one or more synchronous bradycardia pacing modes, such as are described above. One atrial and/or one ventricular sites are designated as rate sites, and paces are delivered to the rate sites based upon pacing and sensed intrinsic activity at the site in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. Multiple synchronized sites may be paced through multiple synchronized sensing/pacing channels, and the multiple synchronized sites may be in the same or different chambers as the rate site.

In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber in accordance with a synchronized pacing mode as described below.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval. FIGS. 2—8 illustrate some of the specific synchronized pacing modes to be described below. A timeline is shown for each channel, with the channels designated as RC for rate chamber, SC for synchronized chamber, ARC for atrial rate chamber, ASC for atrial synchronized chamber, VRC for ventricular rate chamber, and VSC for ventricular synchronized chamber. In each channel, paces are designated as P, inhibited paces are designated as P*, pseudo-paces are designated as P+, and senses are designated as S.

Figure 2:
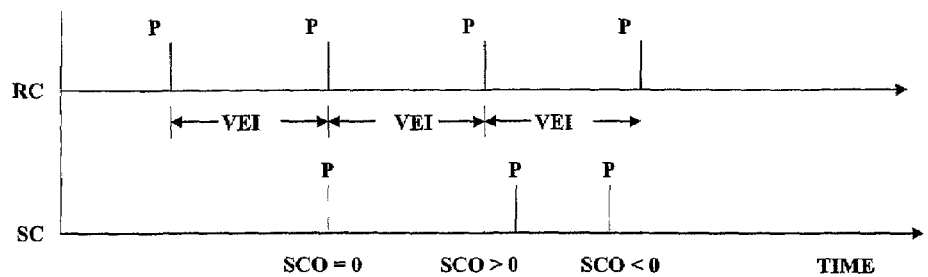
FIGS. 2 through 8 illustrate timing diagrams of different synchronized pacing modes.

FIG. 2 is an example of single-chamber bradycardia pacing with resynchronization, illustrating zero, positive, and negative synchronized chamber offset intervals (SCO). The VEI is defined as the interval between the rate chamber paced events while the SCO is defined as an offset of the synchronized chamber (SC) pace from the rate chamber (RC) pace. Negative and positive offset intervals between 0–120 ms may benefit some patients with severe left or right bundle branch conduction delays and heart dilatation.

Figure 3:
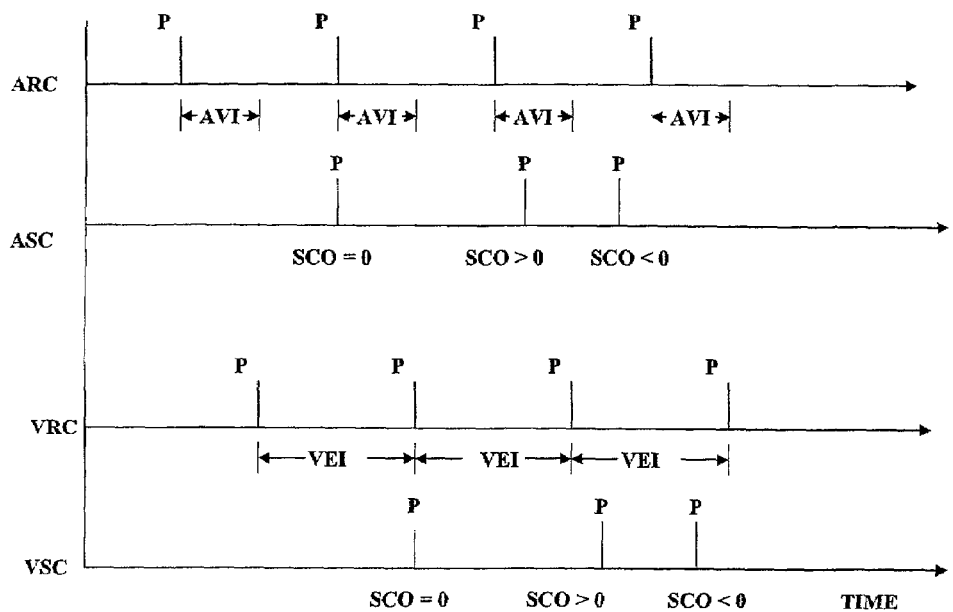
Figure 4:
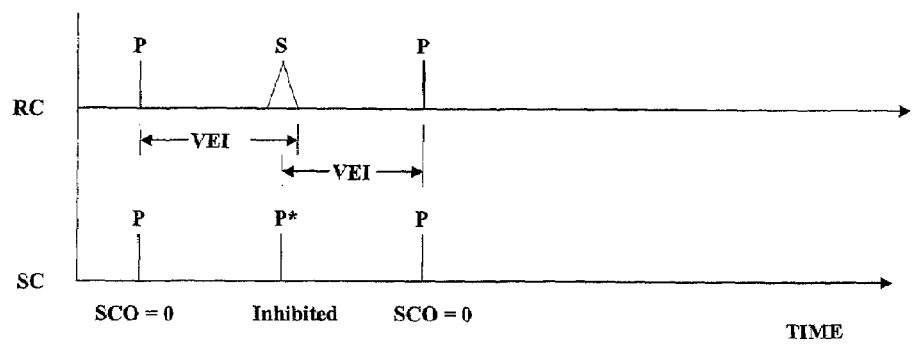

FIG. 3 is an example of dual-chamber bradycardia pacing with resynchronization and various SCOs. The VEI is defined in this case as the interval between the ventricular rate chamber paced events and the AVI is defined as the interval between the atrial and ventricular rate chamber paced events. The SCO for the atrium is defined as an offset of the atrial synchronized chamber and rate chamber paces and the SCO for the ventricle is defined as an offset of the ventricular synchronized chamber and rate chamber paces. The atrial and ventricular SCOs can be independently programmed. FIG. 4 is another illustration of the offset synchronized pacing mode in which the second synchronized chamber pace is inhibited by the rate chamber sense. The rate chamber sense resets the VEI of the rate chamber and the next scheduled synchronized chamber pace.

In the preferred embodiment, pacing in the paired rate and synchronized chambers cannot be inhibited or reset during the SCO interval. Thus, if SCO>0, then after the rate chamber pace occurs, the synchronized chamber pace is committed to occur after the SCO interval. Conversely, if SCO<0, then after the synchronized chamber pace occurs, the rate chamber pace is committed to occur after the SCO interval. Committed SCO pacing can be implemented by controller logic that ignores any sensing events detected in either paired chamber during the SCO interval (i.e., a concurrent sensing refractory period), or the SCO interval can be associated with a concurrent sensing blanking period, during which time sensing in either paired chamber is disabled.

Figure 5A:
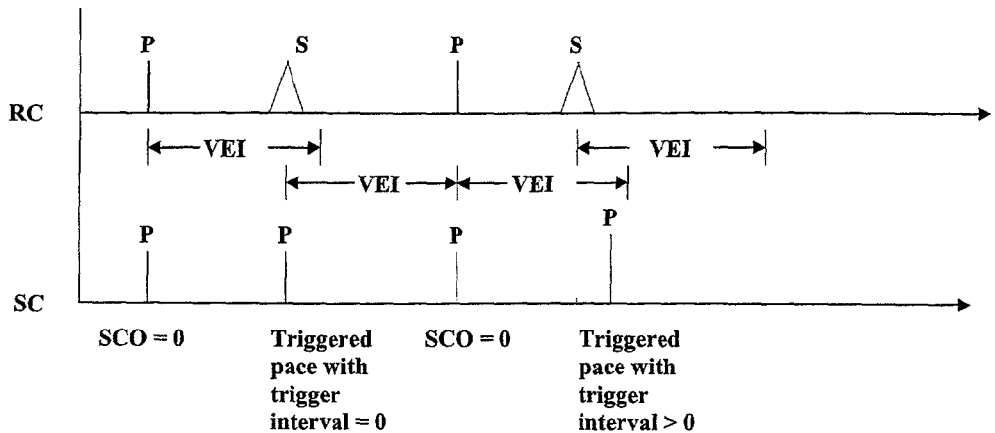
Figure 5B:
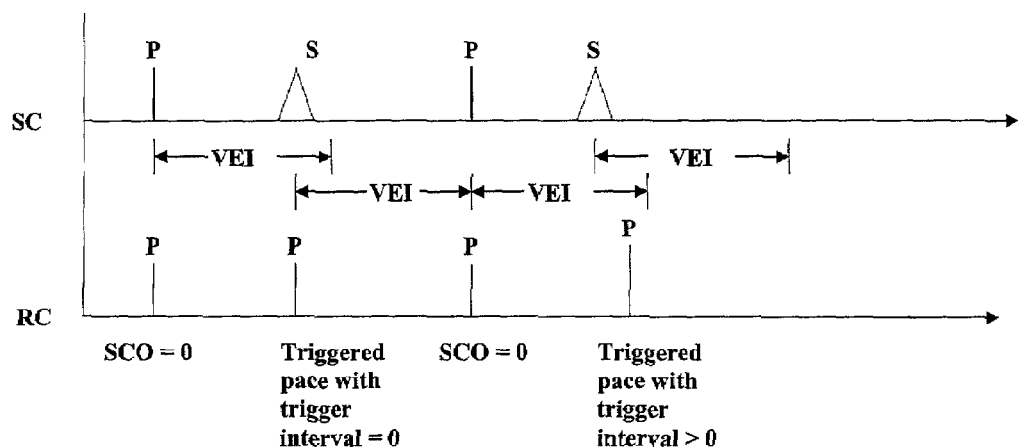

Another resynchronization mode is triggered synchronized pacing. In one type of triggered synchronized pacing, the synchronized chamber is paced after a specified trigger interval following a sense in the rate chamber, as illustrated in FIG. 5A with a trigger interval of zero at the first RC sense and a non-zero trigger interval at the second RC sense. In another type, the rate chamber is paced after a specified trigger interval following a sense in the synchronized chamber as illustrated in FIG. 5B, with a trigger interval of zero at the first SC sense and a non-zero trigger interval at the second SC sense. The two types may also be employed simultaneously. For example, with a trigger interval of zero, pacing of one chamber is triggered to occur in the shortest time possible after a sense in the other chamber in order produce a coordinated contraction. (The shortest possible time for the triggered pace is limited by a sense-to-pace latency period dictated by the hardware.) The triggered synchronized pacing mode may be desirable when an abnormal intra-chamber conduction time is long enough that the pacemaker is able to reliably insert a pace before depolarization from one chamber reaches the other. In another case, it may be desirable to delay triggered pacing of the synchronized chamber with a non-zero trigger interval to mimic the normal physiological conduction delay between the two chambers. For example, when the left atrium pacing is triggered by a sensed depolarization in the right atrium, a non-zero trigger interval can reproduce a physiologically appropriate interatrial conduction delay.

Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of the mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

Figure 6:
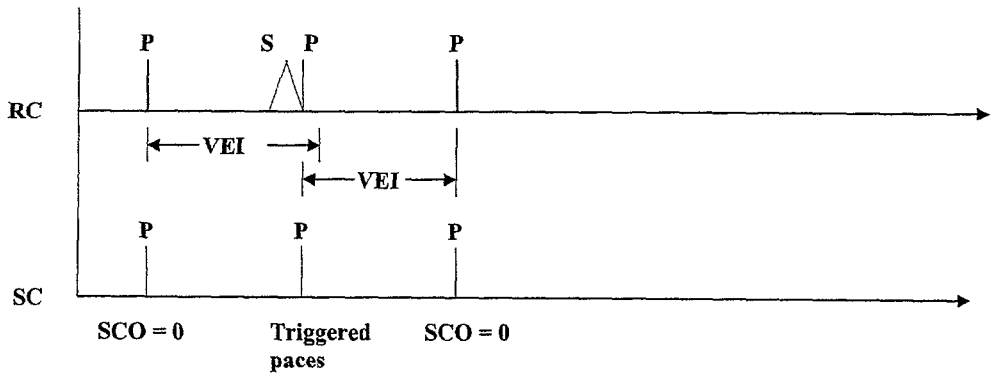
Figure 7:
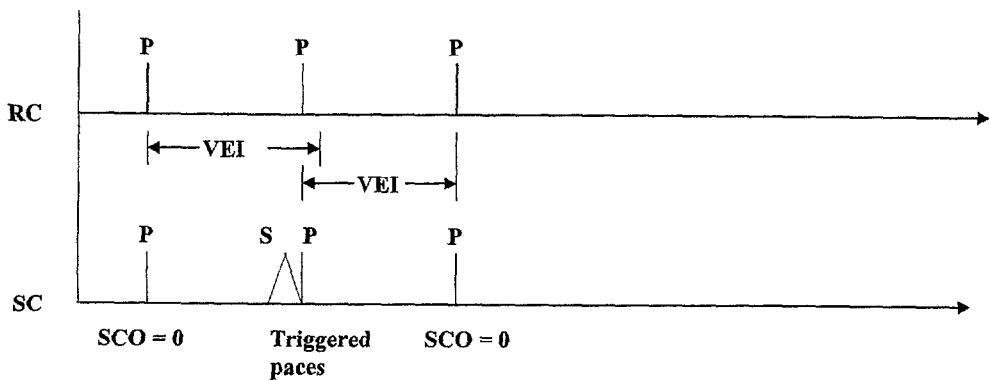

In a variation of the type of triggered synchronized pacing in which the rate chamber is paced after a trigger interval following a sense in the synchronized chamber, a pace is also triggered immediately to the synchronized chamber, such as is illustrated in FIG. 7. The advantage of this is that the sensed event in the synchronized chamber sensing channel might actually be a far-field sense from the rate chamber, in which case the synchronized chamber should be paced to coordinate with the rate chamber depolarization. If the synchronized chamber sense were actually from that chamber, the synchronized chamber pace would occur during that chamber's physiological refractory period and cause no harm. Similarly, in a triggered synchronized pacing mode in which the synchronized chamber is paced after a trigger interval following a sense in the rate chamber, a pace may be also triggered immediately to the rate chamber as illustrated in FIG. 6. One way of implementing this mode is to control the rate chamber by a triggered bradycardia mode so that a sense in the rate chamber sensing channel, in addition to triggering a pace to the synchronized chamber, also triggers an immediate rate chamber pace and resets any rate chamber escape interval. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right ventricular sense were actually from the right ventricle, the right ventricular pace would occur during the right ventricle's physiological refractory period.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pace the synchronized chamber and pseudo-pace the rate chamber immediately before expiration of any rate chamber escape intervals, where a pseudo-pace is a zero energy or virtual pace used to trigger or terminate timing events within the pacemaker. The pseudo-pace thus inhibits a rate chamber pace and resets any rate chamber escape intervals. Such pseudo-pacing can be combined with the offset synchronized pacing mode using a negative offset to pace the synchronized chamber and simultaneously pseudo-pace the rate chamber before expiration of the rate chamber escape interval. The result is that only the synchronized chamber is paced. One advantage of this combination is that sensed events in the rate chamber will inhibit the synchronized chamber-only pacing, which may benefit some patients by preventing pacing that competes with intrinsic activation (i.e., fusion beats). Another advantage of this combination is that rate chamber pacing can provide backup pacing when in a synchronized chamber-only pacing mode, such that when the synchronized chamber pace is prevented, for example to avoid pacing during the chamber vulnerable period following a prior contraction, the rate chamber will not be pseudo-paced and thus will be paced upon expiration of the rate chamber escape interval. Synchronized chamber-only pacing can be combined also with a triggered synchronized pacing mode, in particular with the type in which the synchronized chamber is triggered by a sense in the rate chamber. One advantage of this combination is that sensed events in the rate chamber will trigger the synchronized chamber-only pacing, which may benefit some patients by synchronizing the paced chamber contractions with premature contralateral intrinsic contractions.

Figure 8B:
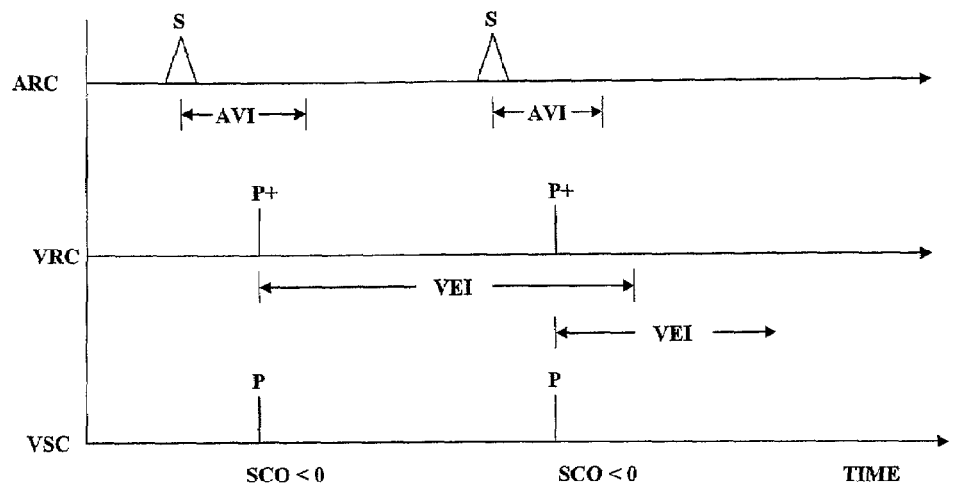
Figure 8A:
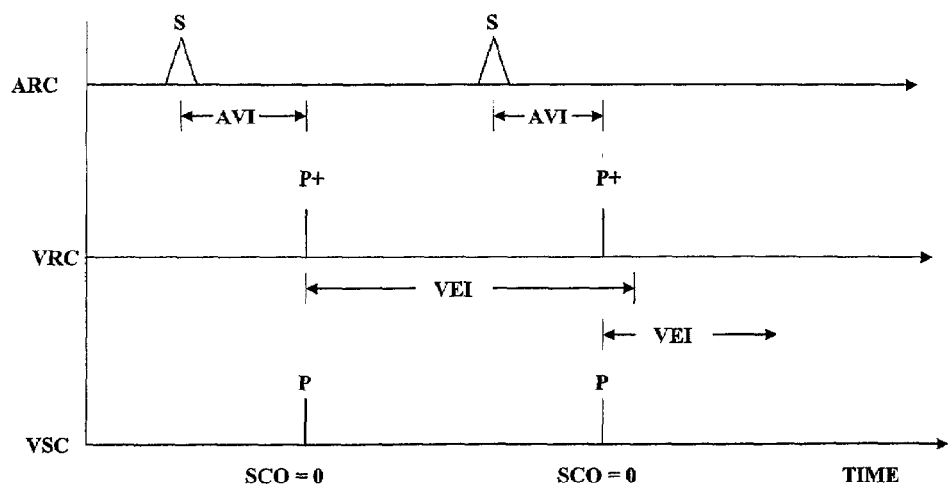
Figure 8C:
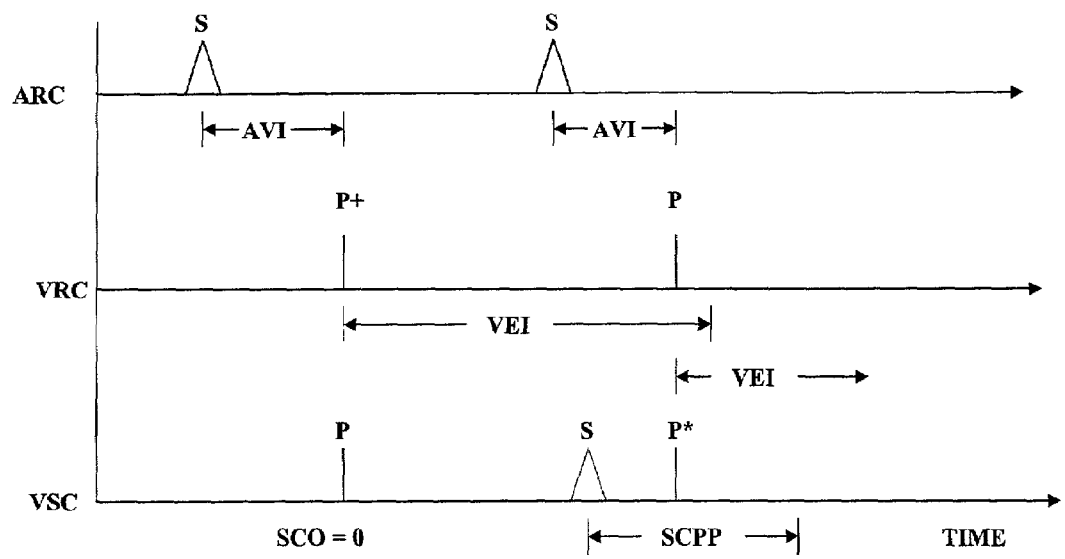

Synchronized chamber-only pacing is illustrated in FIGS. 8A–C for a dual chamber pacing mode. In FIG. 8A, an atrial rate chamber (ARC) sense triggers an AVI, at the end of which a ventricular rate chamber (VRC) pace would be delivered, but which is inhibited by the ventricular synchronized chamber (VSC) pace at zero synchronized chamber offset (SCO) and simultaneous VRC pseudo-pace. FIG. 8B is similar, but illustrates timing with SCO<0. In FIG. 8C, an SC sense occurs, initiating a synchronized chamber protection period (SCPP; see later section) that inhibits the second scheduled VSC pace, which in turn allows the VRC pace to occur in the same cycle. With SCO>0, the rate chamber is paced first so the synchronized chamber pace does not reset rate chamber pacing. One clinical use of synchronized chamber-only pacing is to synchronize paced pre-excitation of the synchronized chamber with intrinsic activation of the rate chamber. This will be most effective with a dual-chamber pacing mode, where the synchronized chamber is a ventricle delayed by bundle branch block and the paired ventricular rate chamber is normally activated by intrinsic atrioventricular conduction. Then the AVI and SCO are set as in the examples of FIGS. 8A–C to pace the ventricular synchronized chamber so that paced and intrinsic activation of the ventricles combine in a beneficial way.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

Synchronized pacing may be applied to multiple sites of a single chamber. In these resynchronization modes, one sensing/pacing channel is designated as the rate channel for sensing/pacing a rate site, and the other sensing/pacing channels in either the same or the contralateral chamber are designated as synchronized channels for sensing one or more synchronized sites. Pacing and sensing in the rate channel follows rate chamber timing rules, while pacing and sensing in the synchronized channels follows synchronized chamber timing rules as described above. The same or different synchronized pacing modes may be used in each synchronized channel.

4. Synchronized Chamber Protection Period

In the resynchronization modes described above, the rate chamber is synchronously paced with a mode based upon detected intrinsic activity in the rate chamber, thus protecting the rate chamber against paces being delivered during its vulnerable period. In order to provide similar protection to the synchronized chamber, a synchronized chamber protection period (SCPP) may be provided. The SCPP is a programmed interval which is initiated by a sense or pace occurring in the synchronized chamber during which paces to the synchronized chamber are inhibited. An SCPP can be implemented in synchronized pacing modes where the rate chamber and the synchronized chamber are either of the ventricles or either of the paired atria. Also, in a multi-site synchronized pacing mode, a protection period can be provided for each synchronized channel.

For example, if the right ventricle is the rate chamber and the left ventricle is the synchronized chamber, a left ventricular protection period LVPP is triggered by a left ventricular sense which inhibits a left ventricular pace which would otherwise occur before the interval expires. The SCPP may be adjusted dynamically as a function of heart rate and may be different depending upon whether it was initiated by a sense or a pace. The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only pacing, a synchronized chamber pace may be inhibited if a synchronized chamber sense occurs within a protection period prior to expiration of the rate chamber escape interval or synchronized chamber offset interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

Figure 9:
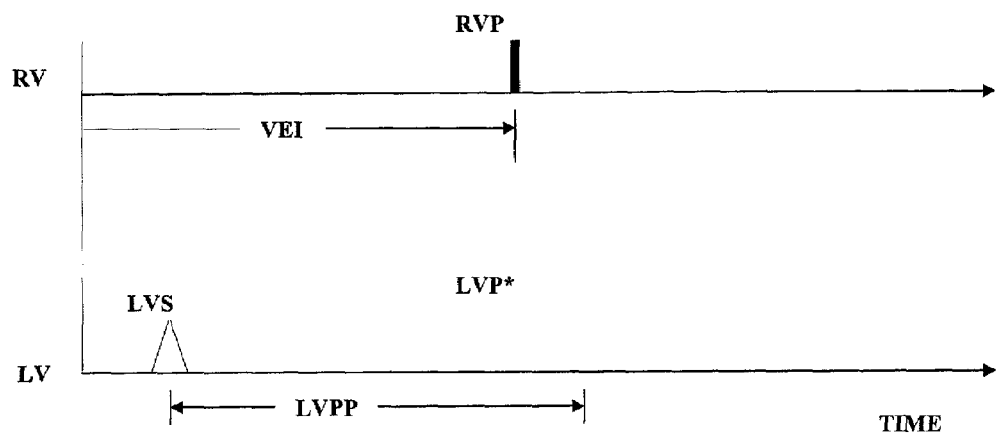
FIG. 9 illustrates a left ventricular protection period implemented with biventricular demand pacing.

FIG. 9 illustrates a left ventricular protection period as implemented with biventricular demand pacing mode with a zero offset and in which the rate and synchronized chambers are the right and left ventricles, respectively. Shown are timelines representing events occurring in the right and left ventricular sensing/pacing channels, designated RV and LV, respectively. A ventricular escape interval, which could be either the lower rate limit interval or the atrio-ventricular delay interval following an atrial sense or pace, is shown as beginning at some earlier time. A left ventricular sense LVS occurs sometime during the ventricular escape interval VEI and initiates the left ventricular protection period LVPP. When the ventricular escape interval expires, a right ventricular pace RVP is delivered. Because the left ventricular protection period has not yet ended, however, the scheduled left ventricular pace is inhibited as designated by LVP*. After the left ventricular protection period expires, a left ventricular pace is permitted to be delivered when the next ventricular pacing instant occurs.

Figure 10:
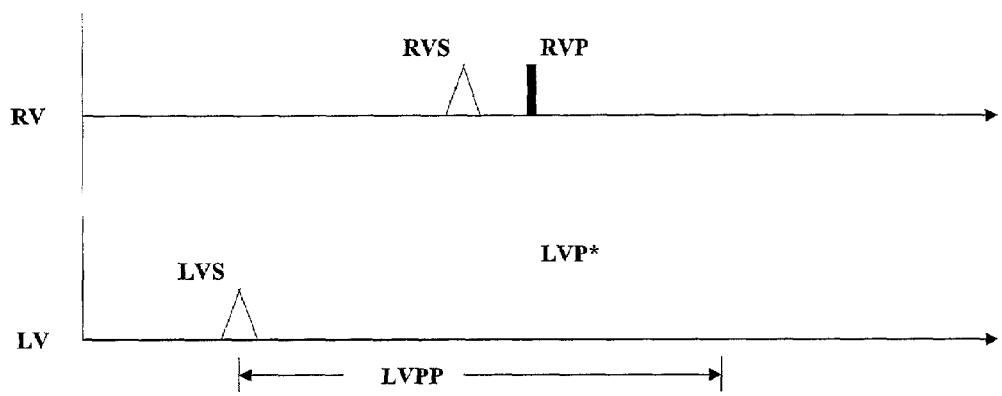
FIG. 10 illustrates a left ventricular protection period implemented with biventricular triggered pacing.

FIG. 10 illustrates the left ventricular protection period as implemented with a ventricular triggered biventricular synchronized pacing mode. Shown are timelines representing events occurring in the right and left ventricular sensing/pacing channels, designated RV and LV, respectively. A left ventricular sense LVS occurs and initiates the left ventricular protection period LVPP. During the LVPP, a right ventricular sense RVS occurs which triggers both a right ventricular and a left ventricular pacing instant. The right ventricular pace RVP is delivered, but, because the left ventricular protection period has not yet ended, a scheduled left ventricular pace is inhibited as indicated by the LVP* marker.

As described above, a protection period may be provided for a synchronized chamber in order to permit the chamber to be safely paced in accordance with escape intervals or triggering events based upon intrinsic activity in the contralateral chamber or distant site in the same chamber. A protection period initiated by a pace or sense at a pacing site can also be advantageously used to safely deliver asynchronous pacing (i.e., pacing not triggered or inhibited by intrinsic activity at the pacing site). For example, a site may be paced at a constant rate (e.g., VOO or AOO), but pacing of the site is inhibited when a pace is scheduled during a protection period initiated by a sense or pace at the site. In another embodiment, the protection period can be used to protect a pacing site that is paced in a rate-adaptive asynchronous mode (VOOR, AOOR) where the pacing rate is controlled by an exertion level sensor.

5. Dynamic Adjustment of Synchronized Chamber Protection Period

As noted above, if the SCPP is set to a programmed value that is estimated to equal or exceed any expected depolarization interval during a paced or intrinsic beat in the synchronized chamber, there will be instances when the actual depolarization interval is less than the SCPP. A scheduled pace to the synchronized chamber is then inhibited when it could have been safely delivered. To overcome this limitation, the length of the SCPP, rather than being set to a programmed value, is dynamically adjusted based upon detection of repolarizations in the synchronized chamber. Such a dynamically adjusted SCPP can be implemented in any of the resynchronization pacing modes described above.

In one embodiment, a repolarization is detected during a paced or intrinsic beat of the synchronized chamber, and the depolarization interval for that beat is measured by measuring the time interval from the pace or sense to the detected repolarization. In the case where the synchronized chamber is a ventricle, the detected repolarization corresponds to a T wave in an EKG, and the depolarization interval corresponds to a Q-T interval. Once a depolarization interval is measured, the SCPP can be adjusted from its programmed initial value to approximate the measured depolarization interval with a possible added safety margin.

Because the measured depolarization interval in any individual is not generally a constant value, different types of depolarization intervals may be used to improve performance. First, the measured depolarization interval in the synchronized chamber may be different during paced and intrinsic beats. It may therefore be desirable for the SCPP to be set to different values depending upon whether the SCPP is initiated by a pace or a sense in the synchronized chamber. In that case, separate types of depolarization intervals are measured during paced and intrinsic beats so that the SCPP can be set accordingly. The depolarization interval may also vary with heart rate. For example, the QT interval generally decreases in normal individuals as heart rate increases. In order to optimally set the SCPP in a manner that takes this into account, depolarization intervals during paced and intrinsic beats are measured at different heart rates. Each such measured depolarization interval is then associated with a particular heart rate so that separate types of depolarization intervals according to heart rate can be used for setting the SCPP. The controller continually monitors the heart rate on a beat-to-beat basis so that, upon delivery of a synchronized chamber pace or detection of a synchronized chamber sense, the SCPP is set to approximately equal the paced or intrinsic depolarization interval measurement that is associated with a heart rate closest to the current heart rate.

Measurements of depolarization intervals as described above may be performed once for each type of depolarization interval that is to be used for setting the SCPP or may be performed periodically to effect a continual updating of the measurements. The latter is generally preferred as it takes into account the possibility that the patient's condition may change over time. Furthermore, there is also the possibility that anomalous measurements may occasionally be obtained that do not reflect the depolarization interval that usually occurs with a paced or intrinsic beat at a given heart rate. To compensate for this, periodic depolarization interval measurements of a given type may be averaged over time to arrive at the value that is to be used in setting the SCPP.

Figure 11:
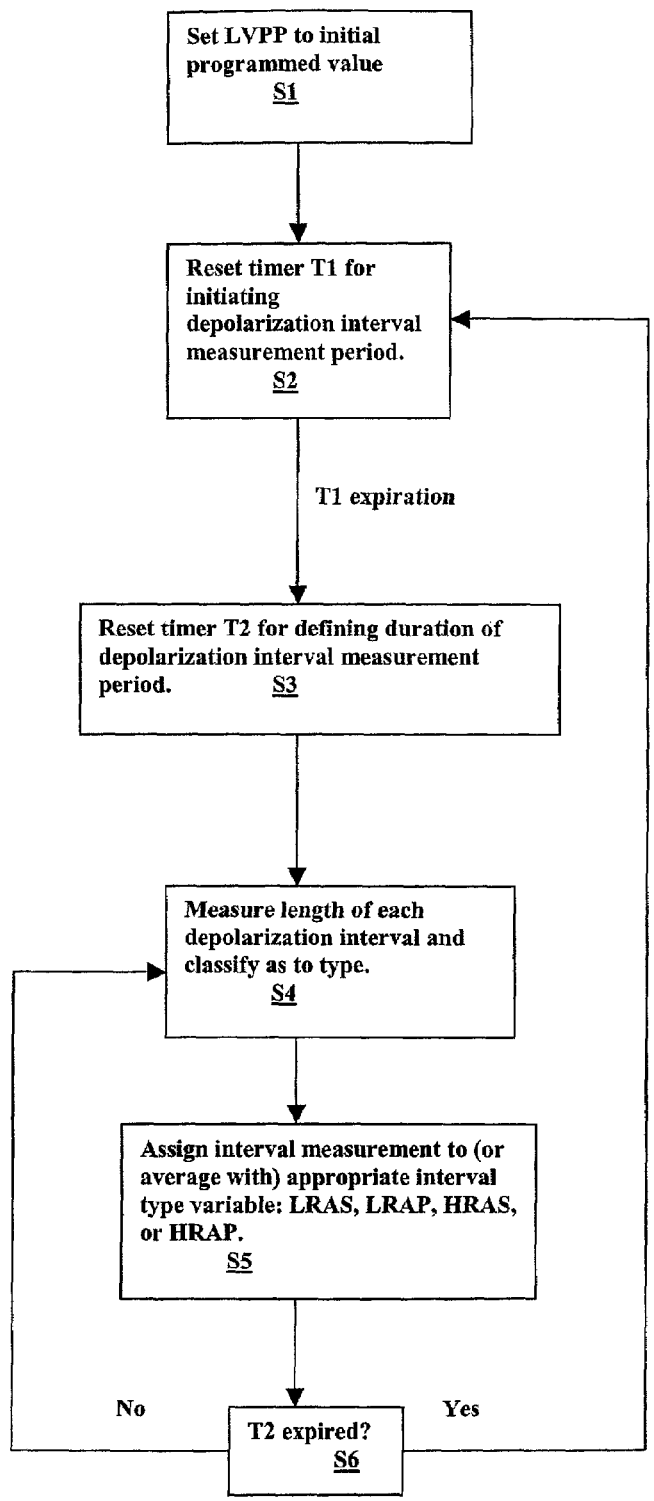
FIG. 11 illustrates an exemplary scheme for implementing dynamic adjustment of a left ventricular protection period.

FIG. 11 illustrates an exemplary scheme for adjusting the SCPP as could be implemented in the programming of the controller 10 of the device in FIG. 1A. In this example, the rate and synchronized chambers are the right and left ventricles, respectively, so that the SCPP is a left ventricular protection period or LVPP. Also, in this example, four types of depolarization intervals are measured and assigned to type variables used to set the LVPP: a low rate depolarization interval after a pace assigned to type variable LRAP, a low rate depolarization interval after a ventricular sense assigned to type variable LRAS, a high rate depolarization interval after a pace assigned to type variable HRAP, and a high rate depolarization interval after a sense assigned to type variable HRAS. A specified rate threshold differentiates a high heart rate from a low heart rate. Other embodiments may employ multiple heart rate zones defined by rate thresholds to define further types of depolarization intervals. At step S1, the controller receives an initial value for the LVPP from the external programmer. This is used by the controller in delivering biventricular pacing until depolarization intervals are measured and assigned to type variables that are used to set the LVPP. A timer T1 defines the periodic (e.g., weekly or daily) initiation of a measurement period during which depolarization intervals are measured and classified as to type. The timer T1 is reset at step S2. Upon expiration of timer T1, a second timer T2 used for defining the duration of the measurement period (e.g., one hour) is reset at step S3. During the measurement period, the depolarization interval of each cardiac cycle is measured at step S4 and classified as being low rate or high rate based upon the detected heart rate and whether the depolarization is due to a sense or pace. The measured and classified depolarization intervals are assigned to one of the depolarization interval type variables at step S5. If a depolarization interval is measured and its type variable has previously been assigned a value, the new measurement may be averaged with the present value of the type variable or a continuous moving average of measurements may be maintained and assigned to the type variable. If the appropriate type value has not yet been assigned a value, the device may continue to use the initially programmed LVPP until a depolarization interval of that type is measured. The measurement period continues until the timer T2 expires as determined at step S6. As the device delivers paces to the left ventricle, the LVPP is set to the value of one of the type variables as determined by the measured heart rate and whether the LVPP was initiated by a sense or pace. A safety margin may be added to the type variable or to the LVPP when it is set to a type variable to ensure that the LVPP will be long enough to cover the T wave.

Figure 12:
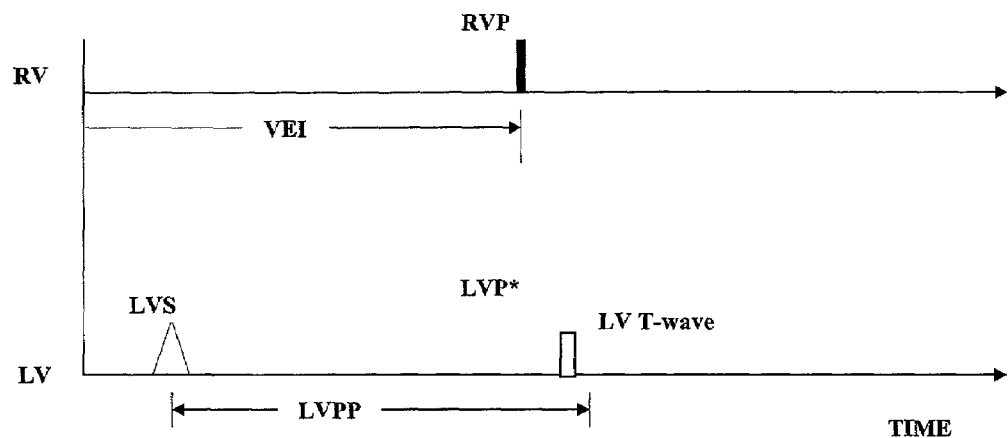
FIG. 12 illustrates a left ventricular protection period that extends beyond a left ventricular repolarization.

FIG. 12 shows a timeline of the right and left ventricular channels where the LVPP is implemented as described above in a biventricular demand pacing mode with a zero offset. A left ventricular sense LVS occurs sometime during the ventricular escape interval VEI and initiates the left ventricular protection period LVPP. The LVPP is set to the type variable appropriate for a post-sense LVPP and for the present heart rate. When the ventricular escape interval expires, a right ventricular pace RVP is delivered. Because the left ventricular protection period has not yet ended, however, the scheduled left ventricular pace is inhibited as designated by LVP*. A repolarization or T wave subsequently occurs in the left ventricle, and the LVPP is shown as extending slightly beyond the T wave before it expires.

Figure 13:
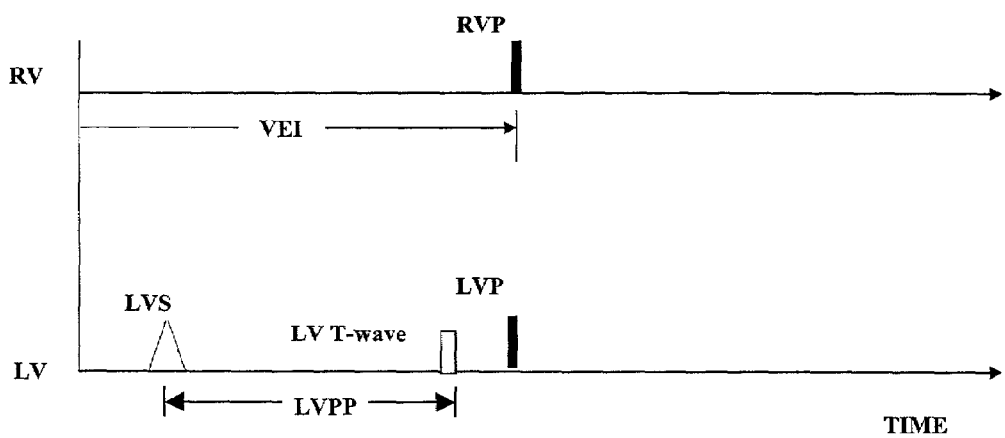
FIG. 13 illustrates a left ventricular protection period that expires upon detection of a left ventricular repolarization.

In another embodiment, the SCPP is dynamically set during each cardiac cycle so that, rather than timing out, it expires upon detection of repolarization in the synchronized chamber. Although it requires more computational overhead to implement, the SCPP is always set to the minimum value with this method. To guard against undersensing of the repolarization, the initially programmed value for the SCPP may be used as a maximum duration so that the SCPP eventually times out if no repolarization is detected. FIG. 13 shows a similar cardiac cycle to that in FIG. 12 but with an LVPP that expires upon detection of a left ventricular T wave. In this case, the left ventricular T wave occurs prior to the left ventricular pacing instant. The LVPP expires at that time so that the left ventricular pace LVP can be delivered.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   sensing channels for sensing intrinsic depolarizations in a rate chamber and a contralateral synchronized chamber and generating sense signals in accordance therewith;
   a controller for controlling the delivery of paces in accordance with a programmed pacing mode;
   wherein the controller is programmed to pace the synchronized chamber in accordance with a synchronized pacing mode in which the synchronized chamber is paced upon expiration of an escape interval, wherein the escape interval is reset by a rate chamber sense or a synchronized chamber pace;
   wherein pacing of the synchronized chamber is inhibited during a synchronized chamber protection period that is initiated by a synchronized chamber sense or pace; and,
   wherein the controller is further programmed to adjust the duration of the synchronized chamber protection period based upon detection of a repolarization in the synchronized chamber.

2. The device of claim 1 wherein the controller is programmed to adjust the synchronized chamber protection period by setting it to approximately equal a measured depolarization interval in the synchronized chamber, the depolarization interval starting with a depolarization in the synchronized chamber and ending with a detected repolarization.

3. The device of claim 2 wherein the controller is programmed to classify measured depolarization intervals as to type depending upon whether the depolarization is due to a sense or pace in the synchronized chamber, with the synchronized chamber protection period being set during each cardiac cycle to approximately equal an appropriate measured depolarization interval in accordance with whether the synchronized protection period is initiated by a sense or a pace.

4. The device of claim 2 wherein the controller is programmed to classify measured depolarization intervals as to type depending upon a measured heart rate, with the synchronized chamber protection period being set during each cardiac cycle to approximately equal a measured depolarization interval whose type corresponds with a presently measured heart rate.

5. The device of claim 2 wherein the controller is programmed to periodically measure depolarization intervals used for setting the synchronized chamber protection period.

6. The device of claim 2 wherein the controller is programmed to average a plurality of measured depolarization intervals.

7. The device of claim 2 wherein the controller is programmed to:
   classify measured depolarization intervals as to type depending upon whether the depolarization is due to a sense or pace in the synchronized chamber, with the synchronized chamber protection period being set during each cardiac cycle to approximately equal an appropriate measured depolarization interval in accordance with whether the synchronized protection period is initiated by a sense or a pace; and, classify measured depolarization intervals as to type depending upon a measured heart rate, with the synchronized chamber protection period being set during each cardiac cycle to approximately equal a measured depolarization interval whose type corresponds with a presently measured heart rate.

8. The device of claim 7 wherein the controller programmed to:
periodically measure depolarization intervals and classify each as to type;
average multiple measured depolarization intervals of the same type; and,
use an initially programmed value for setting the synchronized chamber protection period if a depolarization interval of appropriate type has not yet been measured.

9. The device of claim 1 wherein the synchronized chamber protection period expires during each cardiac cycle upon detection of a repolarization in the synchronized chamber.

10. The device of claim 9 wherein a maximum duration of the synchronized chamber protection period is specified such that the period expires eventually even if no repolarization in the synchronized chamber is detected.

11. A method for operating a cardiac rhythm management device, comprising:
sensing intrinsic depolarizations in a rate chamber and a contralateral synchronized chamber and generating sense signals in accordance therewith;
pacing the synchronized chamber in accordance with a synchronized pacing mode in which the synchronized chamber is paced upon expiration of an escape interval, wherein the escape interval is reset by a rate chamber sense or a synchronized chamber pace;
inhibiting pacing of the synchronized chamber during a synchronized chamber protection period that is initiated by a synchronized chamber sense or pace; and,
adjusting the duration of the synchronized chamber protection period based upon detection of a repolarization in the synchronized chamber.

12. The method of claim 11 further comprising adjusting the synchronized chamber protection period by setting it to approximately equal a measured depolarization interval in the synchronized chamber, the depolarization interval starting with a depolarization in the synchronized chamber and ending with a detected repolarization.

13. The method of claim 12 further comprising classifying measured depolarization intervals as to type depending upon whether the depolarization is due to a sense or pace in the synchronized chamber, with the synchronized chamber protection period being set during each cardiac cycle to approximately equal an appropriate measured depolarization interval in accordance with whether the synchronized protection period is initiated by a sense or a pace.

14. The method of claim 12 further comprising classifying measured depolarization intervals as to type depending upon a measured heart rate, with the synchronized chamber protection period being set during each cardiac cycle to approximately equal a measured depolarization interval whose type corresponds with a presently measured heart rate.

15. The method of claim 12 further comprising periodically measuring depolarization intervals used for setting the synchronized chamber protection period.

16. The method of claim 12 further comprising averaging a plurality of measured depolarization intervals.

17. The method of claim 12 further comprising:
classifying measured depolarization intervals as to type depending upon whether the depolarization is due to a sense or pace in the synchronized chamber, with the synchronized chamber protection period being set during each cardiac cycle to approximately equal an appropriate measured depolarization interval in accordance with whether the synchronized protection period is initiated by a sense or a pace; and,
classifying measured depolarization intervals as to type depending upon a measured heart rate, with the synchronized chamber protection period being set during each cardiac cycle to approximately equal a measured depolarization interval whose type corresponds with a presently measured heart rate.

18. The method of claim 17 further comprising:
periodically measuring depolarization intervals and classify each as to type;
averaging multiple measured depolarization intervals of the same type; and,
using an initially programmed value for setting the synchronized chamber protection period if a depolarization interval of appropriate type has not yet been measured.

19. The method of claim 11 wherein the synchronized chamber protection period expires during each cardiac cycle upon detection of a repolarization in the synchronized chamber.

20. The method of claim 19 wherein a maximum duration of the synchronized chamber protection period is specified such that the period expires eventually expires even if no repolarization in the synchronized chamber is detected.

21. The method of claim 11 wherein right and left ventricles are the rate and synchronized chambers, respectively, and the synchronized chamber protection period is a left ventricular protection period.

22. The method of claim 11 wherein right and left atria are the rate and synchronized chambers.

23. The method of claim 11 further comprising pacing one or more additional synchronized pacing sites in accordance with a synchronized pacing mode based upon rate chamber events and wherein pacing of each synchronized site is inhibited during a synchronized chamber protection period that is initiated by a sense or pace at the synchronized site and that is adjusted based upon detection of a repolarization at the synchronized site.

24. The method of claim 11 wherein the synchronized pacing mode is an offset synchronized pacing mode.

25. The method of claim 11 wherein the synchronized pacing mode is a synchronized chamber-only synchronized pacing mode.

26. The method of claim 11 wherein the synchronized pacing mode is a triggered synchronized pacing mode.

27. The method of claim 11 wherein a pace to the synchronized chamber may be triggered by a synchronized chamber sense and wherein the synchronized chamber protection period starts only after a specified delay from such a triggering event, which allows triggered pacing but prevents pacing during the vulnerable period of the synchronized chamber.

* * * * *

UNITED STATES PATENT AND TRADEMARK OFFICE
CERTIFICATE OF CORRECTION

PATENT NO. : 7,003,347 B2 Page 1 of 1
APPLICATION NO. : 10/172380
DATED : February 21, 2006
INVENTOR(S) : Stahmann It is certified that error appears in the above-identified patent and that said Letters Patent is hereby corrected as shown below:

On Title Page Item (56) under "Other Publications", in column 2, line 2, delete "Remolding" and insert -- Remodeling --, therefor.

On Title Page Item (57), under "Abstract", in column 2, line 11, after "chamber" insert --.--.

Signed and Sealed this

Fifteenth Day of August, 2006

JON W. DUDAS
*Director of the United States Patent and Trademark Office*